US006730286B2

(12) United States Patent
Schramm et al.

(10) Patent No.: US 6,730,286 B2
(45) Date of Patent: May 4, 2004

(54) MANUFACTURING PROCESS TO CONTROL PARTICLE SIZE

(75) Inventors: Ernst Schramm, North Brunswick, NJ (US); Rama K. Narra, North Brunswick, NJ (US); Bruce Kuczynski, Highland Park, NJ (US); Julius P. Zodda, Mercerville, NJ (US)

(73) Assignee: Bracco Diagnostics, Inc., Princeton, NJ (US)

( * ) Notice: Subject to any disclaimer, the term of this patent is extended or adjusted under 35 U.S.C. 154(b) by 335 days.

(21) Appl. No.: 09/795,272

(22) Filed: Feb. 28, 2001

(65) Prior Publication Data

US 2002/0182148 A1 Dec. 5, 2002

(51) Int. Cl.$^7$ .................... A61K 51/00; A61M 36/14
(52) U.S. Cl. ................ 424/1.69; 424/1.29; 424/1.37
(58) Field of Search ................ 424/1.11, 1.29, 424/1.37, 1.69, 9.1

(56) References Cited

U.S. PATENT DOCUMENTS

| | | | |
|---|---|---|---|
| 3,674,900 A | | 7/1972 | Thompson |
| 3,758,678 A | * | 9/1973 | Lindsay et al. ............... 424/1 |
| 3,803,299 A | * | 4/1974 | Nonel ........................ 424/1 |
| 3,862,299 A | | 1/1975 | Bruno et al. |
| 3,863,004 A | | 1/1975 | Wolfangel |
| 3,872,226 A | | 3/1975 | Haney et al. |
| 3,875,299 A | * | 4/1975 | Winchell et al. ............... 424/1 |
| 3,987,157 A | | 10/1976 | Molinski et al. |
| 4,024,233 A | | 5/1977 | Winchell et al. |
| 4,042,576 A | | 8/1977 | Eustache |
| 4,042,677 A | * | 8/1977 | Molinski et al. ............... 424/1 |
| 4,094,965 A | | 6/1978 | Layne et al. |
| 4,187,285 A | | 2/1980 | Meeks et al. |
| 4,333,870 A | | 6/1982 | Koyama et al. |
| 4,410,507 A | * | 10/1983 | Chia et al. ................... 424/1.1 |
| 5,232,828 A | * | 8/1993 | Phi-Wilson et al. ........... 435/2 |
| 5,521,287 A | | 5/1996 | Ohmura et al. |
| 5,589,189 A | * | 12/1996 | Moynihan ................... 424/450 |

* cited by examiner

Primary Examiner—Sreeni Padmanabhan
Assistant Examiner—Lauren Q. Wells
(74) Attorney, Agent, or Firm—Kramer, Levin, Naftalis & Frankel LLP

(57) ABSTRACT

A process for preparing a sterile injectable suspension of radiolabeled macroaggregated serum albumin suitable for use in scanning a mammalian patient consisting of:

1) purifying serum albumin with a saline solution;
2) buffering the purified serum albumin;
3) adding stannous halide in HCl solution to the buffered mixture to obtain a reaction mixture;
4) gradually heating and cooling the reaction mixture to form macroaggregate particles;
5) separating the macroaggregates from the reaction mixture;
6) suspending the macroaggregates in sterile water for injection;
7) adding purified serum albumin;
8) lyophilizing the suspension; and
9) reconstituting the radiolabeled lyophilizate with 99mTc. The invention also includes a process for preparing a stable, sterile lyophilizate of macroaggregate particles of human serum albumin consisting of steps 1–7.

23 Claims, 2 Drawing Sheets

PROCESS FLOW DIAGRAM

MANUFACTURING PROCESS TO CONTROL PARTICLE SIZE

FIELD OF THE INVENTION

This invention relates to a process for preparing a radiopharmaceutical diagnostic agent useful in scanning applications of organs and tissues in a mammal. More particularly, the invention relates to a sterile, stable macroaggregates of human serum albumin suspended in a highly purified, stable human serum albumin carrier in a form which is labeled with technetium-$^{99m}$Tc prior to injecting the human serum albumin into a patient for diagnostic scanning of the lung.

BACKGROUND OF THE INVENTION

Macroaggregated particles of human serum albumin having a particle size of 3 to 150 microns in diameter radiolabeled with technetium-99m have been used in lung function studies and diagnosis. After injection into the patient, the radiolabeled macroaggregated particles diffuse into and are retained by the capillary system of the lung allowing scintigraphic visualization of the vascular system by a diagnostic practitioner. The radiolabeled macroaggregates obstruct the capillaries for only a short time and cause no harm to the pulmonary system. Subsequent to the short retention, the macroaggregates are digested by the phagocytes in the blood thereby clearing the capillaries from the macroaggregates. Technetium-99m, which emits gamma rays, has a radioactive half-life of only about 6 hours and the associated radiation disappears along with the particles of the macroaggregates from the pulmonary system.

A critical characteristic in macroaggregated human serum-containing product is particle size. The product is designed for the macroaggregates to be trapped in the pulmonary capillaries. If embolisms are present in the capillary system, the macroaggregates will not travel through the blockage indicating blood circulatory problems by the lack of radiation from the area of the capillaries where the macroaggregate particles could not enter.

Such blockage may also be caused by macroaggregates too large to pass through certain portions of healthy capillaries thereby indicating inadequate blood circulation or disease. Macroaggregated particles larger than 150 microns in diameter may even block large capillaries. On the other hand, when the macroaggregated particles are smaller than about 3 microns in diameter, they pass through the walls of the capillaries directly into the liver causing shadows and distort the scintiphoto of the lung. (See, for example, U.S. Pat. No. 3,987,157.) To eliminate the problem of artificial blockage of capillaries by large particle size macroaggregates and to prevent passing of small particle size aggregates, the prior art sets a limit on particle size range of about 5 to 10 micron minimum and of about 80 to 100 micron maximum average diameter, while the preferred range is about 15 to 30 micron minimum and 30 to 50 micron maximum in diameter. (See, for example, U.S. Pat. Nos.: 3,674,900; 3,863,004; 3,862,299; 4,024,233; and 4,094,965.)

To obtain macroaggregates of the required particle size, the prior art uses a heating step the temperature of which ranges of from about 70° to 100° C., and a cooling step ranging from about 18° to 22° C.

Although the particle size of the macroaggregates will be in the desired range, the distribution of particle size will vary resulting in a mixture of small, medium and large particles. When radiolabeled, the particles will not carry an even amount of technetium-99m resulting in reduced diagnostic efficacy. Also, the blood flow in the capillaries will preferentially carry the smaller particles, leaving behind the larger particles which travel at a slower rate of speed. This results in a non-uniform distribution of the technetium-99m which influences the scintigraphic reading of the condition of capillaries and tissues. It is, therefore, important to produce macroaggregated particles of essentially uniform size so that the radiolabeled particles will be evenly distributed in the capillaries and tissues and give a reliable reading of maximum diagnostic efficacy on the condition of the pulmonary system.

The prior art also encountered the problem of agglomeration of the particles. U.S. Pat. No. 3,863,004 discloses the labeling of denatured albumin with technetium sulfur colloid which tended to agglomerate on standing and required ultrasonic treatment of the particles prior to use. U.S. Pat. No. 4,187,285 uses an anti-agglomerating surfactant, such as Poloxamer 188, to guard against agglomeration. The ultrasonic treatment suggested in the former patent is cumbersome, while the use of a surfactant suggested in the latter patent is less desirable than a radiolabeled human serum albumin without additives such as a surface active agent.

Commercially supplied albumin is a 25% albumin solution in an aqueous diluent containing additives such as sodium carbonate, sodium citrate and/or acetyltryptophan.

We have discovered that to obtain an efficacious albumin product the commercially available human albumin solution must first be purified prior to proceeding with the aggregating step.

We have also discovered that a technetium-99m labeled human serum albumin product can be made essentially without residual amounts of sodium acetate/acetic acid buffer and hydrochloric acid which are used in the prior art processes.

We have further discovered that particle size can be made essentially uniform by using a controlled heating-cooling cycle when producing the macroaggregates. This enables the control of the number of particles per vial.

We have also discovered that the desired particle size can be further assured by passing the macroaggregates through a size restricting screen to meet USP requirements.

SUMMARY OF THE INVENTION

The process for preparing the injectable suspension of the present invention comprises the steps of:

a) mixing human serum albumin with 0.9% w/v saline solution and ultrafiltering the mixture through a membrane having a porosity of 10,000 nominal molecular weights limit;

b) mixing a buffer having a pH of from 4.95 to 5.25 and adding the buffer to the ultrafiltered mixture to obtain a buffered, ultrafiltered mixture;

c) filtering through a sterile 0.2 micron filter about a 0.43% w/v stannous chloride in HCl solution and adding the solution to the buffered, ultrafiltered mixture to obtain a reaction mixture;

d) heating the reaction mixture gradually so that it attains about 75° C. to 95° C. in about 90 to 100 minutes;

e) cooling the reaction mixture gradually thereby entrapping particles of stannous chloride in the macroaggregates so formed;

f) separating the macroaggregates and resuspending them in sterile water for injection;

g) filtering the resuspended macroaggregates through a 75 micron sterile sizing screen;
h) determining the concentration of the human serum albumin;
i) adjusting the concentration of human serum albumin to the desired dose;
j) transferring the desired volumes into vials and lyophilizing their content; and
k) reconstituting the lyophilized human serum albumin with an aqueous solution of $^{99m}$Tc pertechnate or another isotope of $^{99m}$Tc such as Tc94 or Tc96.

The injectable suspension of the present invention is intravenously administered to a patient for determining the pulmonary blood supply. Following the intravenous administration the $^{99m}$Tc macroaggregated albumin are trapped in functioning pulmonary capillaries and small arterioles. An image of in-vivo radioactivity distribution will then shown the pulmonary lung perfusion.

Although the description herein concerns the use of human serum albumin to form the macroaggregates of this invention, other proteins may be utilized such as, for example, alpha, beta or gamma globulin or fibrinogen.

Figure 1A:
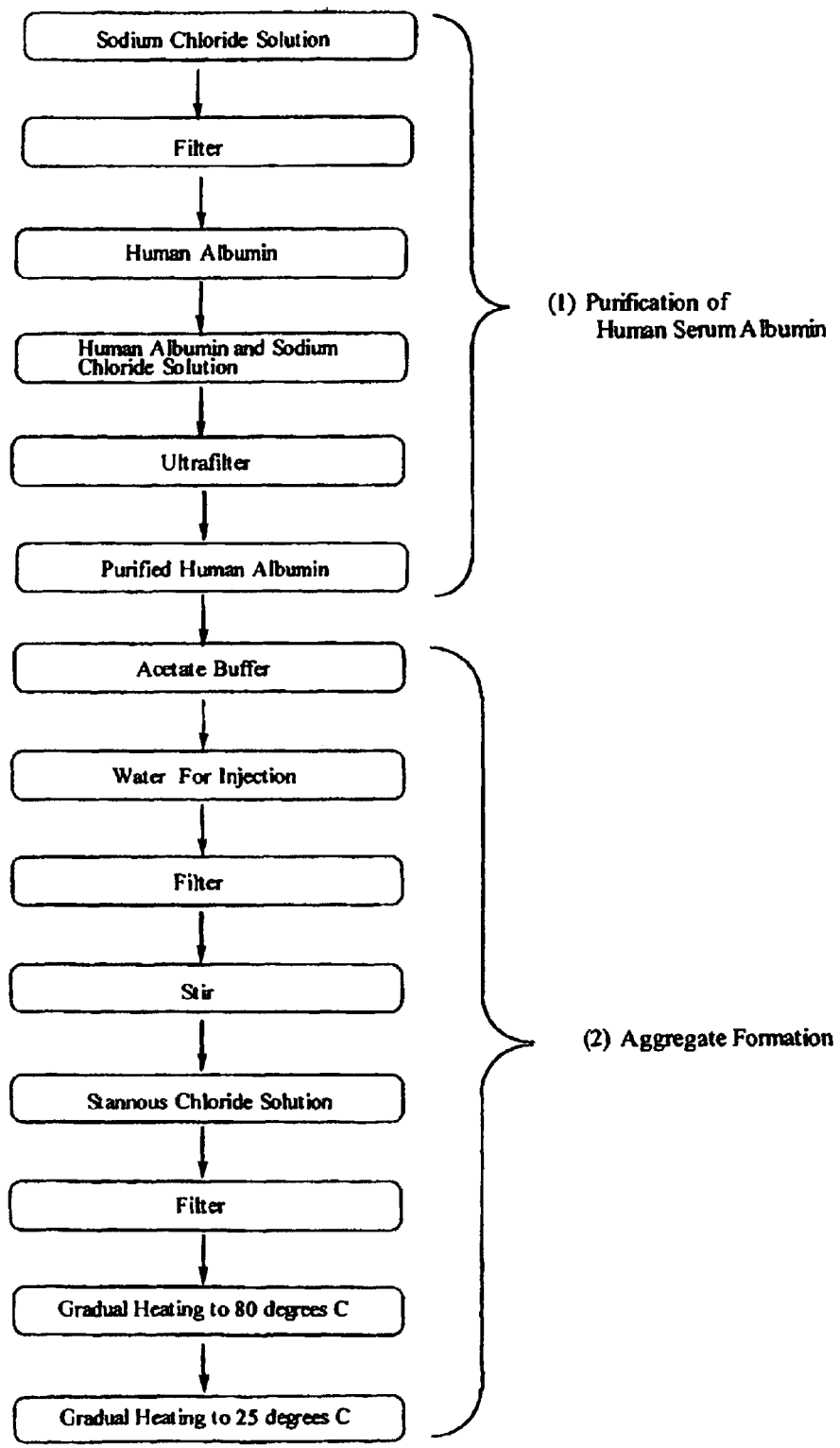
FIGS. 1A and 1B together illustrate a flow diagram of the process of the present invention.
Figure 1B:
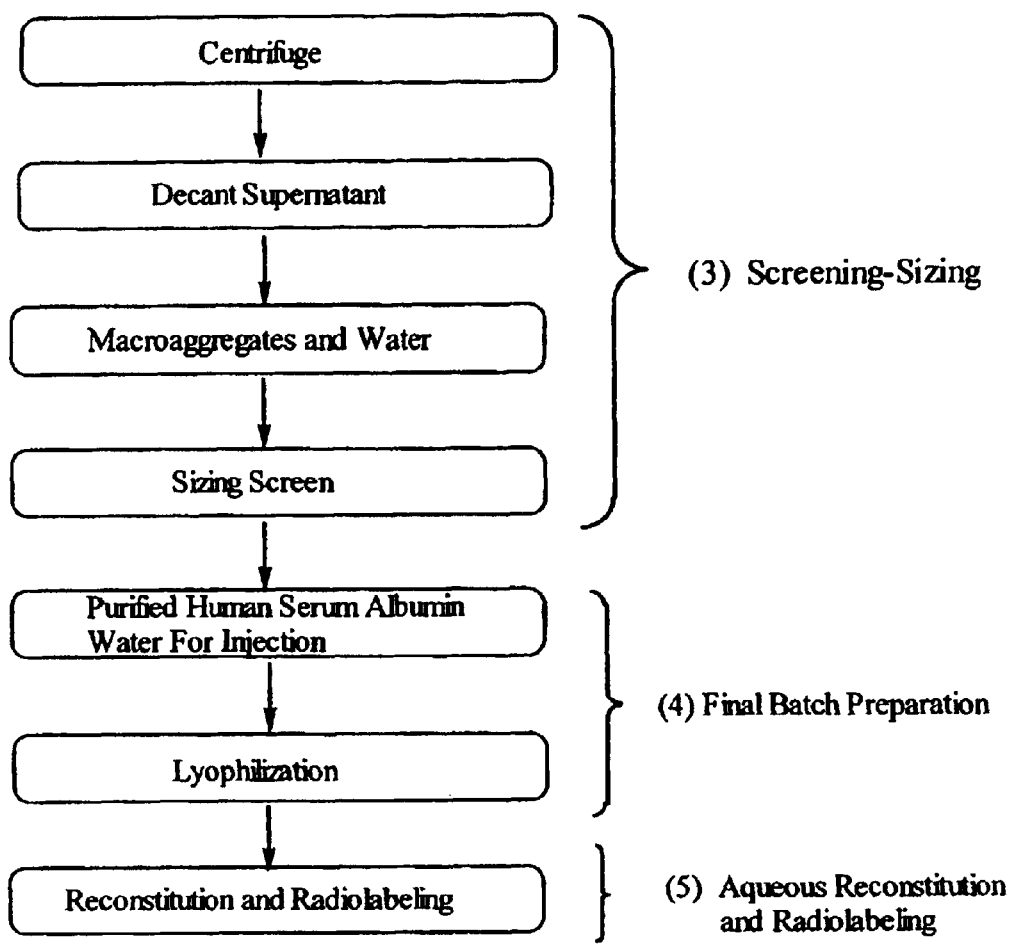

In reference to the flow diagram, there are shown five general categories in the process:

(1) Purification of Human Serum Albumin;
(2) Aggregate Formation;
(3) Screening and Sizing;
(4) Final Batch Preparation; and
(5) Reconstitution and Radiolabeling.

These are discussed in detail in the Detailed Description of the Invention.

DETAILED DESCRIPTION OF THE INVENTION

The present invention is directed to a process for preparing a sterile, injectable suspension of human serum albumin which is radiolabeled with technetium-99m for use in lung scanning diagnostic procedures and the radiolabeled product prepared by this process. The process for preparing the injectable suspension of human serum albumin comprises the steps of:

a) mixing one unit of a 25% w/v human serum albumin with five units of a 0.9% w/v NaCl solution;
b) ultrafiltering the mixture through a membrane having a porosity of 10,000 nominal molecular weight limit using a sufficient volume of 0.9% w/v NaCl solution to purify the human serum albumin;
c) adjusting the volume of the mixture by addition of NaCl solution so that the final concentration of the mixture is about 50 mg of purified human serum albumin/ml of the mixture (5% w/v);
d) adding with stirring to one unit of purified human serum albumin two units of sodium acetate/acetic acid buffer having a pH of from 4.95 to 5.25 and about 3 units of water for injection to obtain a reagent mixture;
e) filtering the reagent mixture through a sterile 0.2 micron filter into a reaction kettle;
f) filtering through a sterile 0.2 micron filter about 2.5 to 3 units of a 0.43% w/v stannous chloride solution in HCl into the reaction kettle to obtain a uniform reaction mixture;
g) heating with stirring the reaction mixture gradually so that it attains about 80° C. in about 100 minutes;
h) cooling with stirring the reaction mixture gradually to about 25° C.;
i) centrifuging the cooled reaction mixture to obtain the macroaggregates and to discard the supernatant;
j) resuspending the macroaggregates in sterile water for injection;
k) passing the resuspended macroaggregates through a 75 micron sterile sizing screen into a sterile calibrated container;
l) determining the protein concentration of the suspension;
m) calculating the batch volume which will have a final protein concentration for the aggregated albumin of 1.5 mg/ml;
n) adding through a 0.2 micron filter sufficient purified albumin (5% w/v albumin) to the batch so that it contains a total of 10 mg/ml purified undenatured albumin;
o) transferring 1.0 ml aliquots into sterile glass vials; and lyophilizing the aliquots to dryness;
p) reconstituting the lyophilized human serum albumin with an aqueous $^{99m}$Tc pertechnate solution or a solution of another isotope of $^{99m}$Tc.

The formulation of the present invention meets all the necessary characteristics in a diagnostic agent useful in scanning applications of organs and tissues in a mammal. The formulation has a lung uptake of 95% and the liver and kidney uptakes are less than 1%. The lyophilized formulation has excellent stability at both 40° C. and at room temperature.

The invention further includes a process for the preparation of a stable, sterile, lyophilizate of macroaggregate particles of human serum albumin suitable for reconstitution and radiolabeling with $^{99m}$Tc pertechnate solution and use in scanning the lungs of a patient and the product prepared by this process. The process for preparing a stable, sterile lyophilizate of macroaggregate particles of human serum albumin comprises steps a) to o) set forth above.

The present invention also includes a process for preparing a sterile injectable solution of macroaggregates suitable for radiolabeling and a product produced by the process. This process comprises the steps of a) to n) described above.

(1) Purification of Human Serum Albumin

Normal human serum albumin (USP) is a sterile preparation of serum albumin obtained by fractionating blood from healthy human donors, not less than 96 percent of its total volume being albumin. It contains certain additives, such as preservatives, so that its shelf-life is extended. In the process of the present invention the normal serum albumin, obtained from commercial sources, is first purified by the use of a sterile filtered 0.9% NaCl (saline) solution: the normal serum albumin is thoroughly mixed with the saline solution, preferably in a 1 to 5 unit ratio, and the mixture is passed through an ultrafiltration system which contains a membrane having a porosity of 10,000 nominal molecular weight limits. In passing the mixture through the membrane, sufficient saline solution is used to purify the human serum albumin. After ultrafiltering, an aliquot is assayed and the concentration is adjusted as desired, preferably to 50 mg of albumin per ml of the solution.

While the invention is described with reference to human serum albumin, it is, of course, contemplated that animal serum albumin, such as cat, horse and other mammalian origin serum albumins, can be similarly purified and subsequent to the process steps constituting the present invention, may be used in the diagnosis of these mammalian species. Additionally, as discussed supra, other proteins such as, for example, alpha, beta or gamma globulin or fibrinogen may be utilized in the process of the instant invention.

(2) Aggregate Formation

The particles of the human serum albumin constituent of the present invention are characterized as macroaggregates which are of irregular shape having an average diameter of between 5 to 100 microns or more.

To form the macroaggregates of the present invention, the purified human serum albumin is first buffered with a suitable buffering agent to a pH of about 4.95 to 5.25, and preferably to the pH of 5.1. Suitable buffering agents are sodium acetate, acetic acid, sodium acid phosphate, disodium phosphate or other art-accepted buffering agents which are readily removable from the final product.

The addition of a stannous salt dissolved in an inorganic acid, such as hydrochloric acid, to the buffered, purified solution of the human serum albumin results in a homogenous mixture of the stannous salt and the purified albumin. The homogeneity of the mixture insures that upon completion of the heating/cooling cycle the stannous salt will bond to the human serum albumin uniformly, i.e., molecule to molecule. Furthermore, this method incorporates the stannous salt within the macroaggregated albumin particle, protecting it from oxidation. This is contrary to a process disclosed, for example, in U.S. Pat. No. 3,863,004, where the macroaggregates already formed are suspended in a buffer solution to which then is added a stannous chloride solution. In this process the stannous chloride complexes with the macroaggregates only on the surface thereof and, depending on the size variation of the macroaggregates, the stannous chloride bound to the surface of the macroaggregates will not be uniformly distributed. This will affect the uniformity of radiolabeling of the macroaggregates and ultimately the radioscanning of the patient.

The purified human serum albumin in a buffer solution mixed to homogeneity with the stannous salt solution constitutes the reaction mixture which is subjected to a heating-cooling cycle in order to form the macroaggregates. The reaction mixture must be heated from room temperature to about 80° C. gradually in about 100 minutes. The rate of heat increase should be about 0.67° C./min. During the heating process the reaction mixture is stirred at about 260 rpm to insure even distribution of heat and uniform aggregation of the purified albumin resulting in a closely controlled particle size range.

Upon attaining about 80° C., the reaction mixture is cooled down, again gradually, to the temperature of 250°±5° C. while stirred at about 260 rpm. The gradual heating/cooling process and controlled stirring rate will result in closely uniform particles of macroaggregates. We have found that this gradual heating/cooling process is contrary to that disclosed in U.S. Pat. No. 4,024,233 where the disclosure calls for rapidly heating the dispersion to a temperature of about 105° C. to 110° C.

The rate of the heating/cooling cycle along with the rate of stirring during the cycle is the controlling factor in both the particle size distribution and the particle size count of the macroaggregates.

(3) Screening and Sizing

At the completion of the heating/cooling cycle the macroaggregate suspension is aseptically centrifuged and the supernatant is discarded. The separated macroaggregates are resuspended using sterile water for injection and passed through a sizing screen so that no larger particle size macroaggregates will pass through the sizing screen than desired. We prefer using a 75 micron sterile sizing screen, however, other sizing screens may be used, such as 60 micron size or lower.

(4) Final Batch Preparation

The protein concentration of the sized suspension is determined by assaying the suspension. Based on the protein concentration found, the batch volume is adjusted so that the desired concentration of mg of aggregated albumin per ml of suspension is achieved.

We prefer to have a final concentration of denatured aggregates of human serum albumin of 1.5 mg per ml of suspension and 10 mg undenatured albumin per ml of suspension. For adjustment of the concentration, 5% w/v purified albumin is added to the suspension using a 0.2 micron filter and nitrogen purged filter sterilized or sterile Water for Injection. These method may be used to obtain other concentrations if different doses are desired for the final product.

Following the concentration adjusting step 1.0 to 1.5 ml aliquots are aseptically transferred into sterile, pyrogen-free glass vials. Sterile, pyrogen-free, fluted stoppers are placed on the vials and their content is lyophilized to dryness. The vials are then flooded with sterile nitrogen, their stoppers are seated, sealed with aluminum or plastic seals and stored at 2° C. to 8° C.

Alternatively, the suspension may be stored at 2° to 8° C. without lyophilization if the suspension is intended to be used within a short time period.

(5) Reconstituting and Radiolabeling

The lyophilized macroaggregates are reconstituted with a sterile, pyrogen-free solution of sodium pertechnate Tc-99m forming a suspension of Tc-99m radiolabeled macroaggregates of human serum albumin. If an unlyophilized macroaggregate suspension is used, the sterile, pyrogen-free solution of sodium pertechnate Tc-99m is added directly to the suspension of macroaggregates. Technetium is a metallic, radioactive synthetic chemical element of atomic number 43. Technetium-99m ($^{99m}$Tc) is a radioisotope of technetium having a half-life of 6.0 hours and emitting primarily gamma rays. $^{99m}$Tc is used in preparations for scanning of organs such as the brain, lung, heart, liver and kidneys. For radiolabeling the suspension of macroaggregates the source of technetium should be water soluble, preferably in the form of sodium pertechnate from a $^{99m}$Tc generator which is well-known in the prior art and is commercially available. Typically, 1 to 3 ml of eluate from a $^{99m}$Tc generator is used to achieve the desired level of radioactivity. This provides up to about 5 to 20 mCi TcO$^-_4$/mg of the macroaggregates. The eluate obtained from the $^{99m}$Tc generator is mixed with the macroaggregate suspension and the mixture is injected into the blood stream of a patient. The dosages will range from about 1 to about 400 $\mu$Ci per kilogram of body weight depending on the nature of the test performed and the nature of the subject on which the test is performed.

For lung scanning a suspension of macroaggregates having 15 to 20 mCi TcO$^-_4$/mg of macroaggregates is preferred. Three to ten minutes after intravenous injection the lungs of the patient contain 90 to 95% of the injected $^{99m}$Tc. Pathological condition, if present, is determined by radioscanning the lungs of the patient and comparing the emission pattern obtained with a standard pattern.

Preferred range of macroaggregates and adjuncts per vial are shown in Table I.

TABLE I

Macroaggretates and Adjuncts Per Vial

| Ingredients | mg/Vial |
|---|---|
| Albumin human, denatured (aggregated) | 0.75–2.25 |
| Tin | 0.05–0.12 |
| Tin as stannous halide (reducing agent) | 0.08–0.18 |
| Purified human serum albumin (carrier) | 5–15 |
| Sodium chloride | 1.5–2.5 |
| Sodium acetate | Trace |
| Acetic acid | Trace |
| Hydrochloric acid | Trace |

Most preferred dosage and adjuncts are shown in Table II.

TABLE II

Most Preferred Dosage and Adjuncts

| Ingredients | mg/Vial |
|---|---|
| Albumin human, denatured (aggregated) | 1.5 |
| Tin | 0.08 |
| Tin as stannous chloride(reducing agent) | 0.13 |
| Purified human serum albumin (carrier) | 10.0 |
| Sodium chloride | 1.8 |
| Sodium acetate | None |
| Acetic acid | None |
| Hydrochloric acid | None |

The following examples illustrate the invention.

EXAMPLE 1

Preparation of Reavents

Water for Injection 20.0 liters of deionized water was added to each of two stainless steel pressure vessels. The vessels were sealed and autoclaved. One vessel was kept at room temperature and the other at 20°–10° C.

Nitrogen Purged Water for Injection

To a 13 liter capacity aspirator bottle 10 liter of Water for Injection was added and nitrogen was bubbled through the water for 30 minutes before use.

0.9% w/v for NaCi Solution 630.0 g of NaCl was dissolved in 70.0 liters of Water for Injection. The solution was sterilized by filtering through a 0.2 micron filter, such as Millipak 60 MPGL or Millidisk 40, into a sterile tank.

Preparation of Purified Albumin (5% w/v Human Albumin)

5 liters of 0.9% w/v NaCl solution was transferred into a graduated 10 liter capacity bottle. One liter of a 25% w/v human serum albumin was added to the bottle and mixed well so that a homogenous solution was obtained. The solution then was recirculated through an ultrafiltration system containing a membrane with a porosity of 10,000 nominal molecular weight limits, using a sufficient volume of 0.9% w/v NaCl solution to purify the human serum albumin. After purification, the volume of the purified human serum albumin was reduced to about 2 liters by ultrafiltration. The purified human serum albumin remaining in the system was recovered using the 0.9% w/v NaCl solution as a rinsing agent. The volume of the albumin solution was adjusted to 4 liters with additional 0.9% w/v NaCl solution and mixed well. An aliquot was taken, assayed, and the final concentration was adjusted to 50 mg/ml (5% w/v) purified human serum albumin with additional 0.9% w/v NaCl solution.

Preparation of 1M (pH 5.10) Acetate Buffer 41.0 g of sodium acetate was dissolved in 300 ml of nitrogen purged Water for Injection. 12 ml of concentrated acetic acid was added and mixed well. The solution was diluted to 500 ml using nitrogen purged Water for Injection. The pH was 5.0.

Preparation of Stannous Chloride Solution 4.30 g of stannous chloride was dissolved in 4.8 ml of concentrated HCl. The solution was diluted to 1 liter with nitrogen purged Water for Injection and mixed well.

The Process of Making the Macroaggregates 351 ml of 1 M (pH 5.1) acetate buffer, 876 ml of nitrogen purged Water for Injection and 613 ml of purified albumin were mixed in a pressure vessel to constitute a reagent mixture which was filtered through a sterile 0.2 micron filter (Millipak 60 MPGL or Millidisk 40) under nitrogen pressure into a sterile reaction kettle. The reagent mixture was stirred for several minutes. While mixing, 640 ml of the stannous chloride solution was then filtered through a sterile 0.2 micron filter under nitrogen pressure, into the sterile reaction kettle, constituting the reaction mixture.

The reaction mixture was heated while being stirred at about 260 rpm from room temperature to 80° C. (±1° C.) in 100 minutes (±5 minutes) using a Computerized Process Controller (CPC). The time/temperature gradient was as shown in Table III:

TABLE III

Time/Temperature Programming Cycle

| Time (Minutes) | Temperature (° C.) |
|---|---|
| 0 | 23 |
| 5 | 25 |
| 10 | 29 |
| 15 | 32 |
| 20 | 36 |
| 25 | 40 |
| 30 | 44 |
| 35 | 47 |
| 40 | 51 |
| 45 | 54 |
| 50 | 57 |
| 55 | 60 |
| 60 | 63 |
| 65 | 66 |
| 70 | 68 |
| 75 | 71 |
| 80 | 73 |
| 85 | 75 |
| 90 | 77 |
| 95 | 79 |
| 100 | 80 |

At the completion of this step the mixture contained the macroaggregates. The stirrer was disengaged, and the reaction kettle containing the macroaggregates was placed into a colling bath containing chilled (2°–10° C.) sterile Water for Injection. The stirrer was reconnected and stirring was resumed at about 260 rpm. When the batch temperature reached 25° C. (±5° C.) the stirring was stopped and the kettle was removed from the bath. At the completion of this step the mixture contained the denatured albumin macroaggreates.

The macroaggreate-containing mixture was transferred into sterile polypropylene centrifuge bottles fitted with screw caps. The mixture was centrifuged at 2500±100 rpm for about 5 minutes. The supernatant was decanted and discarded. The albumin macroaggreates were resuspended in each bottle to 600 ml using sterile Water for Injection as diluent. The resuspended albumin macroaggregates were passed through a 75 micron sterile sizing screen into a sterile calibrated container and the volume of the bulk albumin macroaggregates was adjusted to 3.0 liters using sterile Water for Injection.

The protein concentration, i.e. concentration of macroaggregated albumin was determined and the specific (final batch) volume containing 1.5 mg/ml of the macroaggregated albumin based on the total quantity of macroaggregated albumin present was calculated. Purified human serum albumin was added as a stabilizing agent for the macroaggregates during subsequent lyophilization and to improve shelf storage time. The previously calculated final batch volume was used to determine the quantity of purified albumin required for a final concentration of 10 mg/ml. Sterile Water for Injection and 5% w/v of the purified albumin were added to the suspension by passing the purified albumin through a sterile 0.2 micron filter.

1.0 ml aliquots of the suspension containing the macroaggregates were aseptically transferred to sterile, pyrogen-free vials, fitted with fluted stoppers. The contents of the vials were lyophilized to dryness. The vials were flooded with sterile nitrogen, the stoppers were seated and sealed with aluminum seals.

The product was reconstituted by slowly injecting 1 to 3 ml of sterile $^{99m}$Tc pertechnate solution into the vial containing the lyophilizate and gently shaking the vial in order for the lyophilized material to form a suspension.

Characteristics of the product obtained by the process are shown in Table IV.

TABLE IV

Characteristics of Product

| Characteristics | |
|---|---|
| Number of Particles/Vial | 3 to 10 million |
| Mean Particle Size | 25 ± 5 microns |
| Particle Size Range | >90% between 10 and 90 microns and none greater than 150 microns |
| Pulmonary Clearance (T½) in Rats | <20 hrs |
| Albumin (Excipient) | 10 mg |
| Maximum Radioactivity | 50 mCi |
| Minimum Radioactivity | 10 mCi |
| Maximum Reconstitution Volume | 3 ml |
| Minimum Reconstitution Volume | 1 ml |
| Doses per Vial | 10 |
| Waiting Time After Reconstitution | 5 minutes |
| Storage Conditions After Reconstitution | Refrigerator |
| Shelf Time After Reconstitution | 6.0 hrs |
| Expiration Dating | 9 months |
| Long Term Storage | Refrigerator |
| Radiochemical Purity: | >90% |
| A) Unbound Technetium | <10% |
| B) Supenatant Activity | <10% |
| Biological Efficacy: | |
| Labeled Tc-99m MAA show, at 10 minutes after injection, the following uptake in animals: | |
| Lungs | >95% |
| Liver | <1% |
| Kidneys | <1% |

EXAMPLE 2

Measurements of the important stability indicating parameters, namely the supernatant activity (SA), radiochemical purity (RCP), particle size distribution and mean particle size were performed on three typical batches. The SA and RCP were measured on room temperature (RT) and 40° C. samples at 5 minutes after reconstitution. SA was determined by centrifugation whereby one each of two aliquots of the reconstituted radiolabeled suspension are pipetted into two counting tubes A and B. Tube A is centrifuged followed by removal of the supernatant into a third counting tube C. The radioactivity in tubes B and C are measured and SA is calculated from the equation: %SA=C/B×100.

RCP was determined by ascending paper chromatography whereby the reconstituted radiolabled suspension is spotted about 2 cm from the bottom of a strip of Whatman No. 3 chromatographic paper (origin) and allowed to dry. The strip is developed in an aqueous mixture of 70% methanol by ascending chromatography until the solvent front has traveled about 16 cm from the origin. The strip is allowed to dry and cut 1 cm above the origin. The origin and front portion of the strip are placed into separate counting tubes, A and B, respectively, and the radioactivity is determined. The $^{99m}$Tc bound to albumin will remain in the lower section of the strip at the origin; the unbound $^{99m}$Tc will be in the upper section of the strip. The total radioactivity (C) of the two segments is determined by summation of the radioactivity found in A and B. The RCP is determined from the equation: %Bound $^{99m}$Tc=A/C×100.

The particle size distribution was determined by optical microscopy using a hemocytometer. The longest dimension of not less than 100 particles was measured and the percent of particles within 10–50 micron range was determined. The mean particle size was calculated using the formula:

$$\text{Mean Particle Size } (\mu) = \frac{n_i d_i}{n}$$

where
$n_1$=number of particles within a particular size range;
$d_i$=mid point of the size range; and
n=total; number of particles measured.

The results of these measurements are shown in Table V.

TABLE V

SA, RCP, Particle Size Distribution and Mean Particle Size

| | Storage | | | | | Size/40° C. Storage | |
|---|---|---|---|---|---|---|---|
| Batch | Interval | % S.A. | | % RCP | | Distribution % | Mean |
| Ident. | (months) | RT | 40° C. | RT | 40° C. | in 10–50 $\mu$ | ($\mu$) |
| A | Initial | 0.9 | — | — | — | 99 | 20.6 |
|   | 6.0 | 1.0 | 1.5 | 99.9 | 98.8 | 100 | 22.6 |
| B | Initial | 0.6 | — | — | — | 100 | 21.2 |
|   | 5.5 | 1.0 | 2.3 | 99.9 | 99.8 | 100 | 22.7 |
| C | Initial | 1.0 | — | — | — | 100 | 24.0 |
|   | 4.0 | 1.6 | 1.4 | 99.9 | 99.9 | 100 | 24.8 |

Having described the invention, it is understood that changes and modifications may be effected within the spirit and scope of the invention.

What is claimed is:

1. A process for preparing a sterile, non-pyrogenic injectable suspension of radiolabeled macroaggregate particles of albumin for scanning a mammalian patient comprising the steps of:
   a) mixing serum albumin with 0.9% w/v saline solution and ultrafiltering the mixture through a membrane having a molecular weight cut-off of 10,000;
   b) mixing a buffer having a pH of from 4.95 to about 5.25 with the ultrafiltered mixture to obtain a buffered, ultrafiltered mixture;

c) passing the buffered, ultrafiltered mixture through a sterilizing filter to obtain a sterile mixture;

d) adding a sterile filtered stannous halide in HCl solution to the buffered sterile mixture to obtain a sterile reaction mixture;

e) heating the reaction mixture gradually while stirring continuously so that it attains about 75° C. to 95° C. in about 90 to about 110 minutes;

f) cooling the reaction mixture gradually while stirring continuously so that the macroaggregates containing the stannous halide are formed;

g) separating the macroaggregates from the reaction mixture, resuspending them in sterile water for injection, and filtering them through a sizing screen;

h) adjusting the concentration of the macroaggregates with sterile water for injection and adding sterile, filtered, purified albumin;

i) transferring the suspension into vials for storage and lyophilization;

j) flooding the lyophilized vial with inert gas before sealing the lyophilized vial under an inert gas atmosphere; and k) reconstituting the lyophilized serum albumin with aqueous $^{99m}$Tc pertechnate solution.

2. The process of claim 1 wherein said serum albumin is human serum albumin.

3. The process of claim 1 wherein said buffer is sodium acetate and acetic acid.

4. The process of claim 1 wherein said stannous halide is stannous chloride.

5. The process of claim 1 wherein said heating is at about 80° C. in about 100 minutes.

6. The process of claim 1 wherein said cooling is from about 75°–95° C. to about 25° C. in less than 100 minutes.

7. The process of claim 6 wherein said cooling is from about 75°–95° C. to about 25° C. in less than 30 minutes.

8. The process of claim 1 wherein said sizing screen is about 75 microns.

9. The process of claim 1 wherein said macroaggregates have an average particle size of from 10 to 75 microns.

10. The process of claim 9 wherein said macroaggregates have an average particle size of from 40 to 60 microns.

11. The process of claim 10 wherein said macroaggregates have an average particle size of from 45 to 55 microns.

12. A process for preparing a sterile lyophilizate of macroaggregate particles of human serum albumin for reconstitution and radiolabeling with $^{99m}$Tc for scanning a mammalian patient comprising the steps of:

a) mixing serum albumin with 0.9% w/v saline solution and ultrafiltering the mixture through a membrane having a molecular weight cut-off of 10,000;

b) mixing a buffer having a pH of from 4.95 to about 5.25 with the ultrafiltered mixture to obtain a buffered, ultrafiltered mixture;

c) passing the buffered, ultrafiltered mixture through a sterilizing filter to obtain a sterile mixture;

d) adding a sterile filtered stannous halide in HCl solution to the buffered sterile mixture to obtain a sterile reaction mixture;

e) heating the reaction mixture gradually while stirring continuously so that is attains about 75° C. to 95° C. in about 90 to about 110 minutes;

f) cooling the reaction mixture gradually while stirring continuously so that the macroaggregates containing the staruious halide are formed;

g) separating the macroaggregates from the reaction mixture, resuspending them in sterile water for injection, and filtering them through a sizing screen;

h) adjusting the concentration of the macroaggregates with sterile water for injection and adding sterile, filtered, purified albumin;

i) transferring the suspension into vials for storage and lyophilization; and j) flooding the lyophilized vial with inert gas before sealing the lyophilized vial under an inert gas atmosphere.

13. The process of claim 12 wherein said serum albumin is human serum albumin.

14. The process of claim 12 wherein said buffer is sodium acetate and acetic acid.

15. The process of claim 12 wherein said stannous halide is stannous chloride.

16. The process of claim 12 wherein said heating is at about 80° C. in about 100 minutes.

17. The process of claim 12 wherein said cooling is from about 75° C.–95° C. to about 25° C. in less than 100 minutes.

18. The process of claim 12 wherein said sizing screen is about 75 micron.

19. A process for preparing a stable, sterile lyophilizate of macroaggregate particles of human serum albumin for reconstitution and radiolabeling with technetium-99m and scanning the lungs of a patient comprising the steps of:

a) mixing one part 25% w/v human serum albumin with five parts 0.9% w/v saline solution;

b) ultrafiltering the mixture through a membrane having a molecular weight cut-off of 10,000 using a sufficient volume of 0.9% w/v NaCl solution to purify the human serum albumin; adjusting the volume by ultrafiltration or by addition of the NaCl solution to c) adjusting the volume by ultrafiltration or by addition of the NaCl solution to mixture so that the final concentration of the mixture is about 50 mg of purified human serum albumin/ml of the mixture;

d) adding with stirring to two parts purified human serum albumin one part sodium acetate/acetic and acid buffer having a pH of from 4.95 to 5.25 and about three parts water for injection to obtain a reagent mixture;

e) filtering the reagent mixture through a sterile 0.2 micron filter into a reaction kettle;

f) filtering through a sterile 0.2 micron filter about two parts 0.43% w/v stannous halide solution in HCl into the reaction kettle to obtain a uniform reaction mixture;

g) heating with stirring the reaction mixture gradually so that it attains about 80° C. in about 100 minutes;

h) cooling with stirring the reaction mixture gradually to about 25° C.;

i) centrifuging the cooled reaction mixture to obtain the macroaggregates and to discard the supernatant;

j) resuspending the macroaggregates in sterile water for injection k) passing the resuspended macroaggregates through a 75 micron sterile sizing screen into a sterile calibrated container;

l) determining the protein concentration of the suspension;

m) calculating the batch volume with which will have a concentration for the macroaggregated albumin of 1.5 mg/ml;

n) adding through a 0.2 micron filter sufficient water for injection and purified albumin (5% w/v albumin) to the batch so that it contains a total of 10 mg/ml purified undenatured albumin; and o) transferring 1.0 ml aliquots into sterile glass vials; and lyophilizing the aliquots to dryness and sealing under inert atmosphere.

20. The process of claim 19 wherein said macroaggregates have an average particle size diameter of from 10 to 75 microns.

21. The process of claim 20 wherein said macroaggregates have an average particle size of from 40 to 60 microns.

22. The process of claim 21 wherein said macroaggregates have an average particle size of from 45 to 55 microns.

23. A process for preparing a sterile, non-pyrogenic, injectable suspension of macroaggregate particles of albumin for radiolabeling and scanning a mammalian patient comprising the steps of:

a) mixing serum albumin with 0.9% w/v saline solution and ultrafiltering the mixture through a membrane having a molecular weight cut-off of 10,000;

b) mixing a buffer having a pH of from 4.95 to about 5.25 with the ultrafiltered mixture to obtain a buffered, ultrafiltered mixture;

c) passing the buffered, ultrafiltered mixture through a sterilizing filter to obtain a sterile mixture;

d) adding a sterile filtered stannous halide in HCl solution to the buffered sterile mixture to obtain a sterile reaction mixture;

e) heating the reaction mixture gradually while stirring continuously so that is attains about 75° C. to 95° C. in about 90 to about 110 minutes;

f) cooling the reaction mixture gradually while stirring continuously so that the denatured macroaggregates containing the stannous halide are formed;

g) separating the macroaggregates from the reaction mixture, resuspending them in sterile water for injection, and filtering them through a sizing screen; and h) adjusting the concentration of the macroaggregates with sterile water for injection and adding sterile, filtered, purified albumin.

* * * * *